Aug. 11, 1942. F. H. HOWARD Plant Pat. 539
ROSE PLANT
Filed Dec. 11, 1941
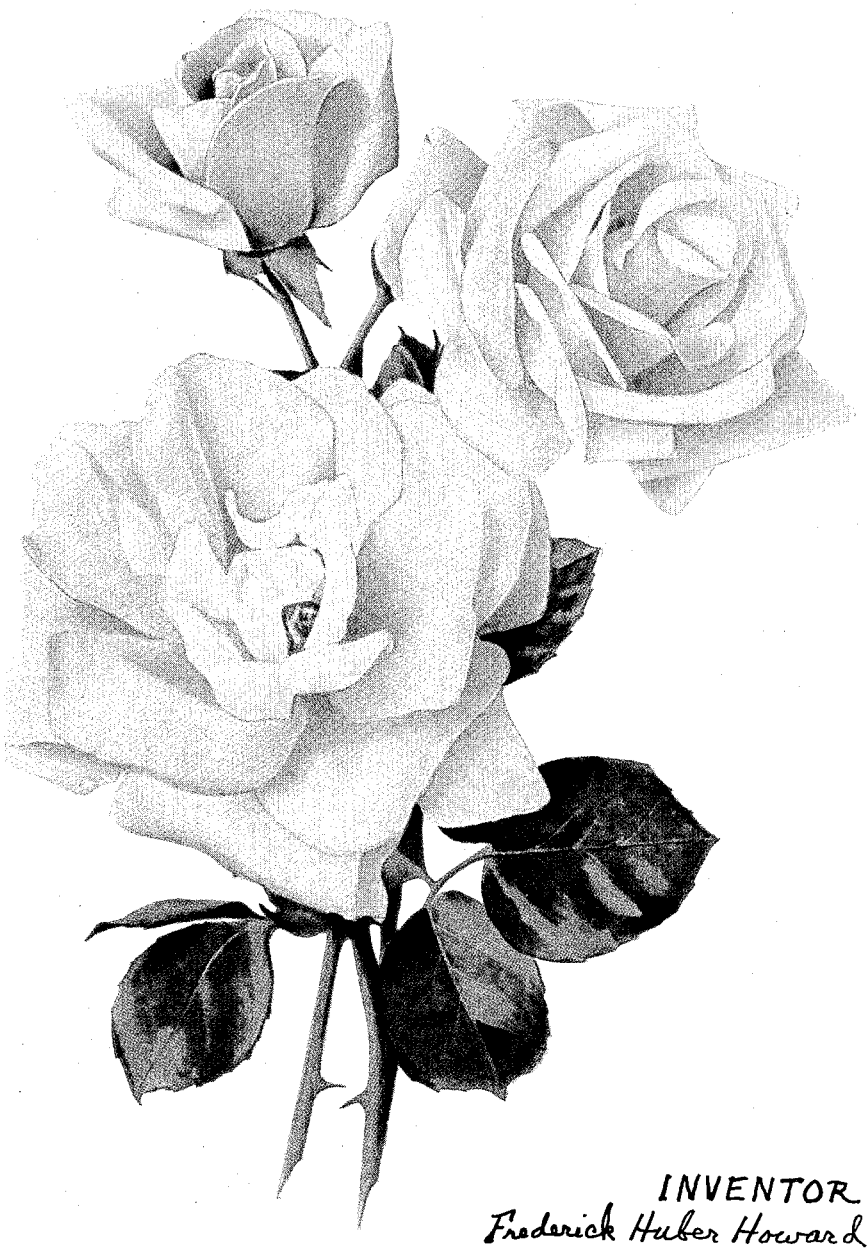
INVENTOR
Frederick Huber Howard
By Orville M Kile
Plant Patent Agt.

Patented Aug. 11, 1942

Plant Pat. 539

UNITED STATES PATENT OFFICE

539

ROSE PLANT

Frederick Huber Howard, Montebello, Calif.

Application December 11, 1941, Serial No. 422,591

1 Claim. (Cl. 47—61)

My present invention relates to a new and distinct variety of hybrid tea rose plant possessing features which in combination make a most desirable rose plan producing an attractive blossom of deep silvery pink. One of the outstanding features of this new variety is its profuse and continuous production of flowers.

My new variety originated as the result of definite breeding efforts carried on by me. The variety Mrs. J. D. Eisele and an unnamed seedling were crossed and the resulting seedling in turn crossed with the pollen of E. G. Hill. It has been asexually reproduced and its distinguishing characteristics have held through succeeding generations.

The original illustration which is filed as a part of this application shows, in approximately true colors, three specimens of this new rose variety in various stages of opening.

In the following detailed description of the plant and flower, color plate references indicate Ridgway's Color Standards and Nomenclature.

*The plant*

Growth: Upright; bushy; 2 to 3 feet in height; stands up well in hot weather.

Blooming habit: Profuse, continuous bloomer during the entire season. Thirty-five or forty blossoms are produced by each plant per year. Blossoms usually borne singly.

Disease resistance: Excellent. Plants grown in California under normal field culture, without any spraying whatever, evidenced absolutely no mildew or blackspot, although in the same field and adjacent to this variety were thousands of other roses some varieties of which were badly affected by mildew and a number of varieties of which showed evidence of blackspot.

Stems: Very stiff and strong; heavy; Calla Green (Plate V); numerous thorns.

*Thorns.*—Medium size; sharp; slightly downward-pointing; irregularly placed on stem; light brown with red tinge.

Foliage: Three to five leaflets.

*Amount.*—Normal.

*Color.*—Dark green, approximately Yew Green (Plate XXXI) on the upper surface, and Light Elm Green (Pl. XVII) on under surface.

*Shape.*—Very broad compared to length, almost round but with sharp-pointed apex.

*Size.*—Terminal leaflets much larger than lateral ones and usually from 1¼ to 1½ inches wide by 1¾ to 2 inches long.

*Rachis.*—Deep-grooved; slender; reddish-tinged; has some small thorns on under side.

*Stipules.*—Short; narrow; clinging except for acute points.

*The flower*

Bud:

*Size.*—Just before calyx breaks it is slightly less than one inch long. As bud begins to unfurl it is 1½ to 1¾ inches long.

*Shape.*—Conical; long-pointed.

*Opening.*—Slow and even.

*Peduncle.*—Wiry; strong; short, thus bringing foliage close to flower.

*Sepals.*—Wide and relatively short, about ⅜ inch wide at base and about 1 inch long. Mostly simple, with only few small branches. Seldom foliaceous. Do not reflex in bud stage.

Blossom:

*Size.*—Medium. Grown in the open, measures about 3½ to 4 inches in diameter when fully open.

*Form.*—High-centered at first, finally opening into a deep, open cup-shape with central petals considerably shorter and smaller than outer petals and the many large brilliant stamens visible.

*Petalage.*—In October the usual number of petals is from 20 to 23.

*Color.*—The color is a uniform soft silvery rose or deep pink, approximately the same on both surfaces and rather evenly distributed. The Ridgway color which would most nearly describe it lies between Rose Color (Pl. XII) and Spinel Pink (Pl. XXVI), although even this would not give a true idea of the silvery tone. The outer petals are slightly lighter on their edges. There is a large center of bright yellow stamens which makes a vivid contrast in the open flower.

Petals:

*Shape.*—Outer petals are almost round with a very slight point at top of some of them and slight waviness at edges of some. Rather deeply cupped.

*Size.*—Outer petals are about 1¾ inches by 2 inches; inner petals much smaller.

*Arrangement.*—Regular; superimposed.

*Behavior.*—Drop cleanly, oftentimes all petals dropping from flower at one time.

Fragrance: Mild and pleasing.

Longevity: Exceptionally good both on bush and as cut flower.

Reproductive organs:

*Pistils.*—Many; tightly bunched, protruding from center of a large, high pithy ring. *Style*—White at base, upper half-red-tinged. *Stigma*—Greenish white.

*Stamens.*—Many, edging large pithy ring around pistils. *Filaments*—Rose or red-tinged. Slightly shorter than pistils. *Anthers*—Large; bright yellow, approximately Light Cadmium (Plate IV).

Having thus disclosed my invention, I claim:

The new and distinct variety of hybrid tea rose with combination of characters substantially as herein shown and described, characterized particularly by its profuse and continuous production of bloom; its resistance to blackspot and mildew; its ability to stand up well in hot weather; and its medium sized bloom with exceptional keeping qualities, good form and distinctive uniform color of silvery rose or deep pink as indicated.

FREDERICK HUBER HOWARD.